United States Patent [19]
Thompson

[11] Patent Number: 6,007,484
[45] Date of Patent: Dec. 28, 1999

[54] ENDOSCOPE HAVING ELEVATION AND AZIMUTH CONTROL OF CAMERA

[75] Inventor: Robert Lee Thompson, Dallas, Tex.

[73] Assignee: Image Technologies Corporation, Rogers, Ark.

[21] Appl. No.: 09/065,116

[22] Filed: Apr. 23, 1998

Related U.S. Application Data

[63] Continuation of application No. 08/937,238, Sep. 16, 1997, Pat. No. 5,762,603, which is a continuation of application No. 08/708,044, Aug. 30, 1996, abandoned
[60] Provisional application No. 60/003,802, Sep. 15, 1995.

[51] Int. Cl.⁶ ...................................................... A61B 1/05
[52] U.S. Cl. ........................ 600/173; 600/122; 600/129; 600/138
[58] Field of Search .................................... 600/102, 103, 600/109, 114, 122, 129, 137, 160, 170, 171, 173, 112, 121; 348/82–85, 65, 143, 144, 155, 206; 165/11.2

[56] References Cited

U.S. PATENT DOCUMENTS

| | | |
|---|---|---|
| 3,557,780 | 1/1971 | Sato . |
| 3,896,793 | 7/1975 | Mitsui et al. . |
| 3,958,080 | 5/1976 | Schadler . |
| 4,697,210 | 9/1987 | Toyota et al. . |
| 4,718,417 | 1/1988 | Kittrell et al. . |
| 4,741,326 | 5/1988 | Sidall et al. . |
| 4,791,479 | 12/1988 | Ogiu et al. . |
| 4,819,620 | 4/1989 | Okutsu ..................................... 600/114 |
| 4,855,838 | 8/1989 | Jones et al. . |
| 4,858,001 | 8/1989 | Milbank et al. ......................... 600/170 |
| 4,905,082 | 2/1990 | Nishigaki et al. . |
| 4,947,827 | 8/1990 | Opie et al. . |
| 4,971,035 | 11/1990 | Ito . |
| 4,989,586 | 2/1991 | Furukawa ..................................... 128/6 |
| 5,028,997 | 7/1991 | Elberbaum . |
| 5,111,288 | 5/1992 | Blackshear . |
| 5,166,787 | 11/1992 | Irion . |
| 5,217,453 | 6/1993 | Wilk . |
| 5,237,984 | 8/1993 | Williams, III et al. . |
| 5,243,967 | 9/1993 | Hibino et al. . |
| 5,251,613 | 10/1993 | Adair . |
| 5,267,970 | 12/1993 | Chin et al. . |
| 5,271,381 | 12/1993 | Ailinger et al. . |
| 5,290,168 | 3/1994 | Cooper et al. . |
| 5,305,121 | 4/1994 | Moll . |
| 5,307,804 | 5/1994 | Bonnet . |
| 5,308,325 | 5/1994 | Quinn et al. . |
| 5,334,150 | 8/1994 | Kaali . |
| 5,349,941 | 9/1994 | Hori . |
| 5,351,678 | 10/1994 | Clayton et al. . |
| 5,368,015 | 11/1994 | Wilk . |
| 5,380,291 | 1/1995 | Kaali . |
| 5,381,784 | 1/1995 | Adair . |
| 5,381,943 | 1/1995 | Allen et al. . |
| 5,383,859 | 1/1995 | Sewell, Jr. . |
| 5,396,879 | 3/1995 | Wilk et al. . |
| 5,402,768 | 4/1995 | Adair . |
| 5,418,567 | 5/1995 | Boers et al. ............................. 348/143 |
| 5,458,132 | 10/1995 | Yabe et al. . |
| 5,483,951 | 1/1996 | Frassica et al. . |
| 5,489,256 | 2/1996 | Adair . |
| 5,508,735 | 4/1996 | Mueller . |
| 5,531,664 | 7/1996 | Adachi et al. . |
| 5,538,497 | 7/1996 | Hori . |
| 5,540,649 | 7/1996 | Bonnell et al. . |
| 5,558,619 | 9/1996 | Kami et al. . |
| 5,573,494 | 11/1996 | Yabe et al. . |
| 5,591,192 | 1/1997 | Privietera et al. . |
| 5,617,762 | 4/1997 | Kirsch ..................................... 348/143 |
| 5,626,553 | 5/1997 | Frassica et al. . |
| 5,689,365 | 11/1997 | Takahashi ............................... 600/166 |

FOREIGN PATENT DOCUMENTS

| | | |
|---|---|---|
| 78 33 379 | 11/1978 | Germany . |
| 9113080 | 1/1992 | Germany . |
| 23 25 24 | of 0000 | Japan . |
| WO 96/10947 | 4/1996 | WIPO . |

*Primary Examiner*—John P. Leubecker
*Attorney, Agent, or Firm*—Wolf, Greenfield & Sacks, P.C.

[57] ABSTRACT

A surgical/diagnostic imaging device for use in interabdominal, interthoracic, and other surgical and diagnostic procedures includes an image sensor pivotally mounted at the distal end of a support. In use, the image sensor and support are contained within a disposable sterile sheath, and the distal portion of the sheath is inserted into the patient through an incision. The imaging device includes actuators to move the image sensor in elevation and azimuth.

23 Claims, 5 Drawing Sheets

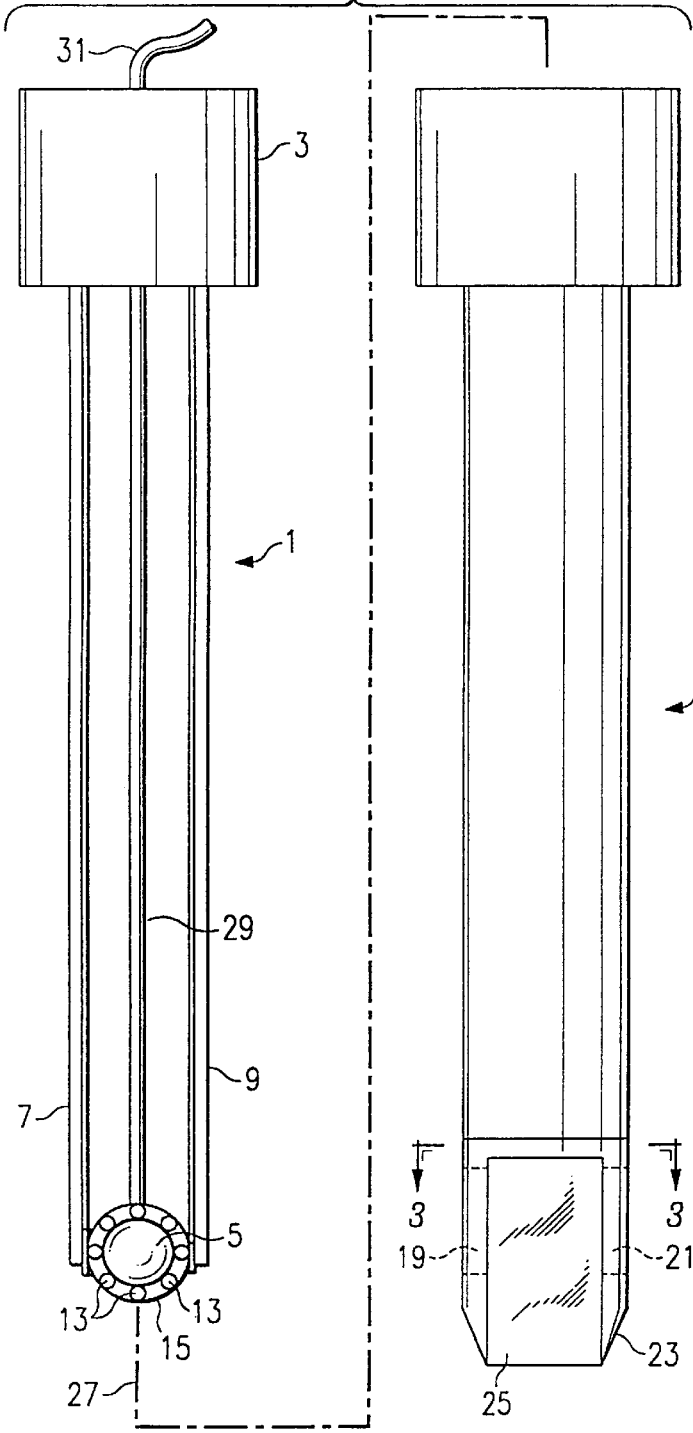
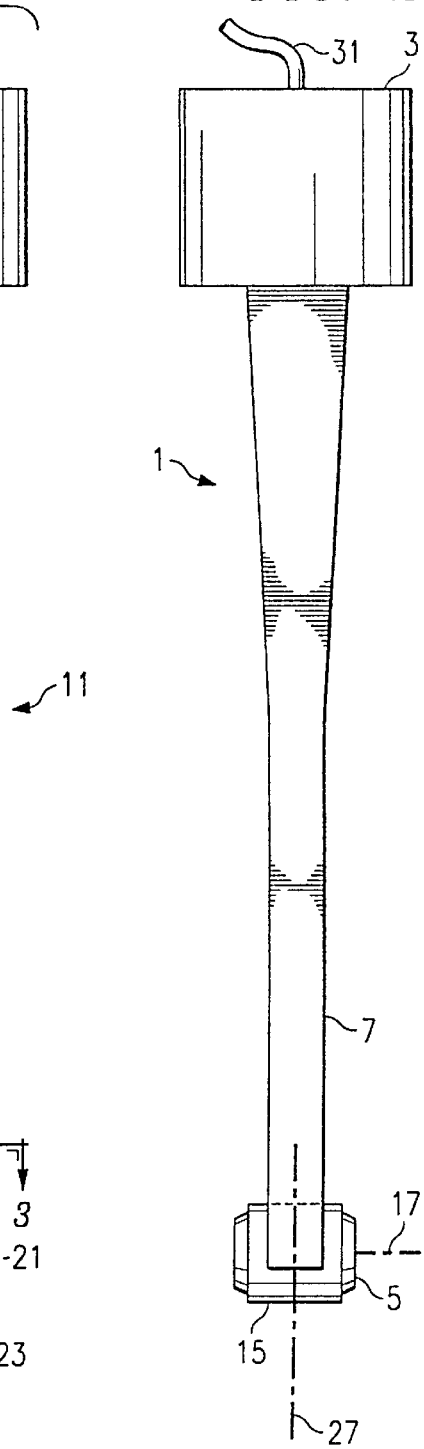
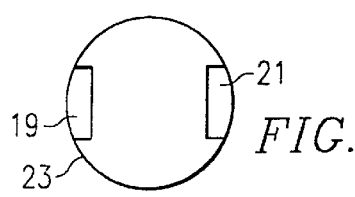
FIG. 1
FIG. 2
FIG. 3

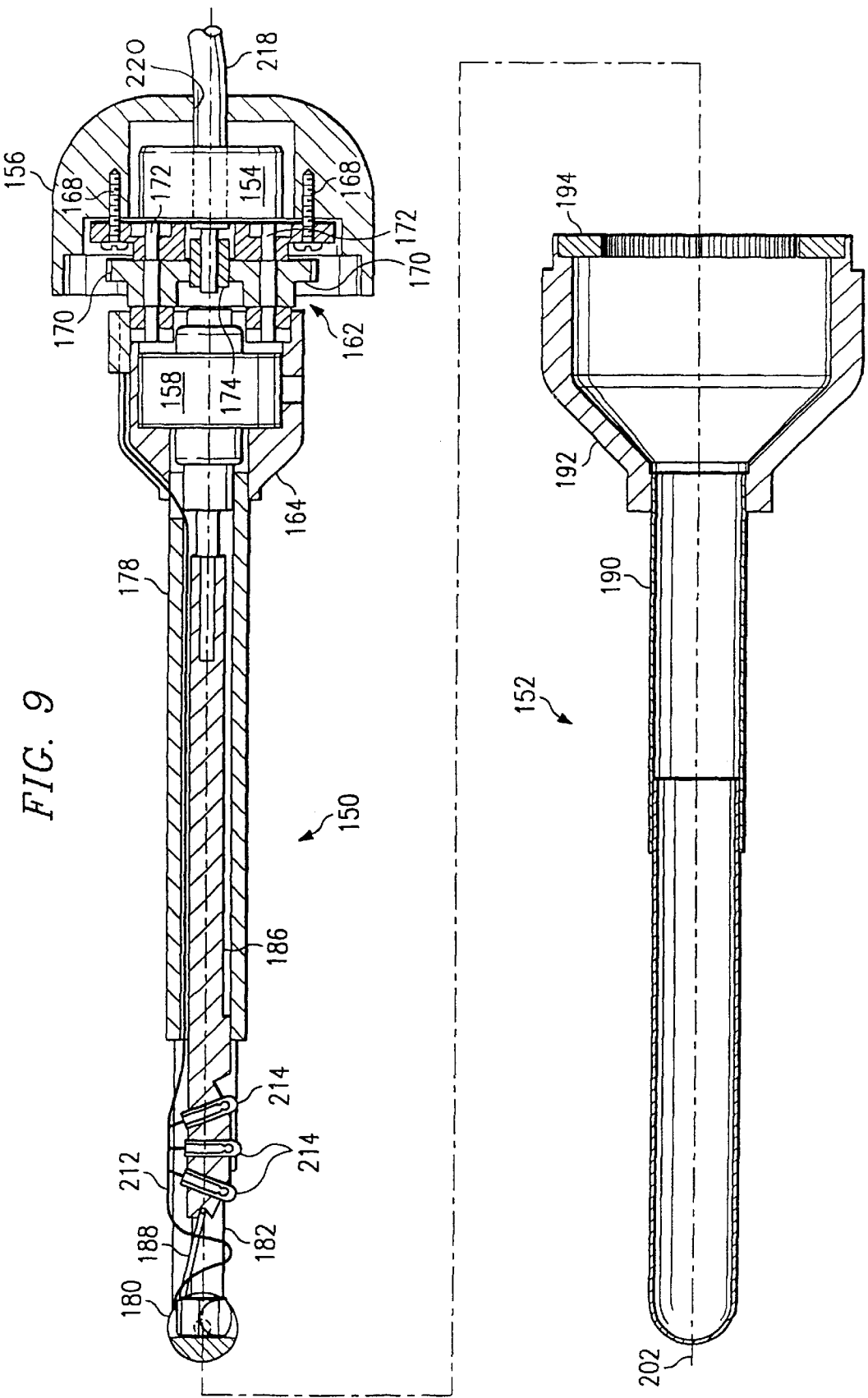

ENDOSCOPE HAVING ELEVATION AND AZIMUTH CONTROL OF CAMERA

This application is a continuation of application Ser. No. 08/937,238, filed Sep. 16, 1997, and now U.S. Pat. No. 5,762,603, which is a continuation of application Ser. No. 08/708,044, filed Aug. 30, 1996, now abandoned, which claims the benefit of Provisional Application No. 60/003,802, filed Sep. 15, 1995.

TECHNICAL FIELD OF THE INVENTION

This invention is related to an imaging device for use in interabdominal, interthoracic, and other surgical and diagnostic procedures on the human body.

BACKGROUND

Endoscopic surgery and diagnosis are considerably less invasive than the conventional procedures. This results in a lower mortality rate and minimizes both the patient's hospital stay and recovery time.

Conventional endoscopes include a rigid elongated member, a lens assembly, and an imaging device mounted either on or within the endoscope. Examples of such endoscopes are described in U.S. Pat. Nos. 4,697,210 (Toyota et al.), 4,791,479 (Ogiu et al.), and 4,989,586 (Furukawa).

Although a conventional endoscope can be constructed to have a wide field of view, the picture quality suffers. As a practical matter, the field of view of conventional endoscopes must be relatively narrow. As a result, a conventional endoscope must be positioned carefully at the beginning of a procedure, then held in position throughout the procedure, which generally requires the full-time attention of one member of the operating team. U.S. Pat. No. 5,351,678 (Clayton et al.) addresses the initial positioning problem by providing an endoscope having a distal end which is offset from the endoscope's longitudinal axis. With the Clayton et al. endoscope, the surgeon can easily change the area viewed by rotating the endoscope about its longitudinal axis. However, the Clayton et al. endoscope must still be held in place throughout the procedure by a member of the operating team.

SUMMARY OF THE INVENTION

A surgical/diagnostic imaging device embodying the invention includes a charge-coupled device ("CCD") and an associated lens mounted within a camera bore in a camera housing. The camera housing is pivotally mounted at the distal end of an elongated camera support. High intensity lights are also mounted within bores in the camera housing that are coaxial with the camera bore and thus with the axis of the CCD.

Prior to use, the camera housing and camera support tube are inserted into a disposable sterile sheath. The distal portion of the sheath is then inserted into the patient through an incision in the patient. Electric stepper motors and associated components are provided to move the camera housing (and thus the CCD) in elevation and azimuth.

The imaging device is electrically connected to a control console. The control console is in turn electrically connected to a display device and a control assembly. The display device displays the image received by the CCD and the control assembly allows the surgeon to control the elevation and azimuth of the camera housing.

The surgical/diagnostic imaging device is easily aimed at the area of interest within the patient by the surgeon. In addition, surgical/diagnostic imaging device need not be held in position in the patient by a member of the operating team.

BRIEF DESCRIPTION OF THE DRAWINGS

An embodiment of the invention will be described, by way of example only, with reference to the accompanying drawings, in which:

FIG. 1 is a front view of a surgical/diagnostic imaging device in accordance with the invention;

FIG. 2 is a partially cutaway side view of the imaging device of FIG. 1;

FIG. 3 is a cutaway top view of the sheath cap taken through plane 3—3 in FIG. 1;

FIG. 9 is a cutaway side view of a second imaging device in accordance with the invention;

DETAILED DESCRIPTION

Figure 4:
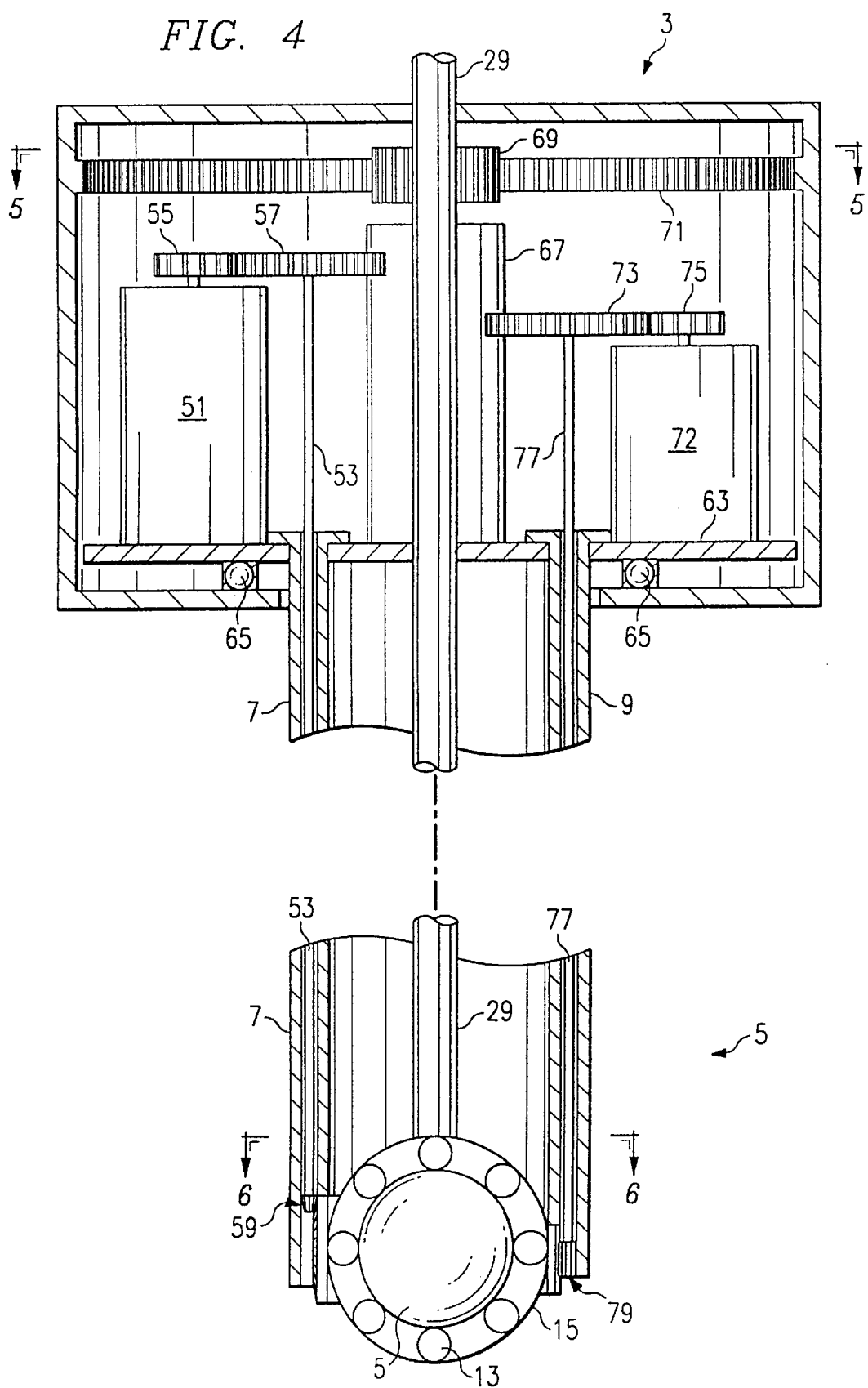
FIG. 4 is an enlarged cutaway side view of the upper housing and the lower portion of the imaging device.

FIGS. 1–3 show a surgical/diagnostic imaging device 1 for use in interabdominal, interthoracic, and other surgical and diagnostic procedures. The device 1 comprises an upper housing 3, a camera housing 5, and left and right camera housing supports 7, 9. Before use, the device 1 is inserted into a sterile sheath 11. The device 1 and sheath 11 (collectively, the "camera") are then inserted through an incision (not shown) into the patient's body (not shown). The camera is inserted so as place the camera housing 5 in a position from which it can be pointed at the surgical site or the area to be diagnosed. The incision is sealed around the camera with a purse string stitch, thereby preventing leakage of the $CO_2$ gas which is used to distend the patient's abdomen or chest during surgery or diagnosis.

In this embodiment, the sheath 11 is constructed of medical-grade plastic is provided in a sterilized condition, and is intended to be disposed of after use. Alternately, the sheath 11 can be constructed of heat-resistant materials in order to allow it to be sterilized using an autoclave, then reused. It should be appreciated that the sterile sheath 11 eliminates the need to sterilize the camera.

The camera housing 5 contains a CCD (not shown) and a zoom lens assembly (not shown). A plurality of high intensity lights 13 are mounted within a light housing 15 which extends about the outer circumference of the camera housing 5. The lights 13 are aligned with the focal axis 17 of the CCD, and they provide illumination of the area at which the camera housing 5 and hence the CCD are pointed.

When the device 1 is inserted in the sheath 11, the left and right camera housing supports 7, 9 engage complimentary locking keys 19, 21 within a sheath cap 23. As a result, the camera housing 5 is locked into a position in which the CCD's focal axis 17 is aligned perpendicular to an optically-clear window 25. In addition, as will be described below in connection with FIGS. 4–6, the locking keys 19, 21 cause the sheath cap 13 to rotate about the longitudinal axis 27 of the camera when the camera housing supports 7, 9 are rotated about that axis.

A camera cable 29 extends between the camera housing 5 and the upper housing 3. The camera cable 29 contains conductors which carry the CCD's signals to the upper housing 3 and which supply electrical power to the CCD and lights 13. An imaging device cable 31 is provided to carry control signals and supply electrical power to the device 1 and to carry the CCD's signals to external processing and display devices (not shown).

The length of the camera housing supports 7, 9 and the length of the sheath 11 are varied to accommodate variation in the thickness of the abdominal walls of patients and to allow the camera to be used in thoracic surgery/diagnosis. Three lengths are provided: 3, 6, and 11 inches below the upper housing 3.

Figure 5:
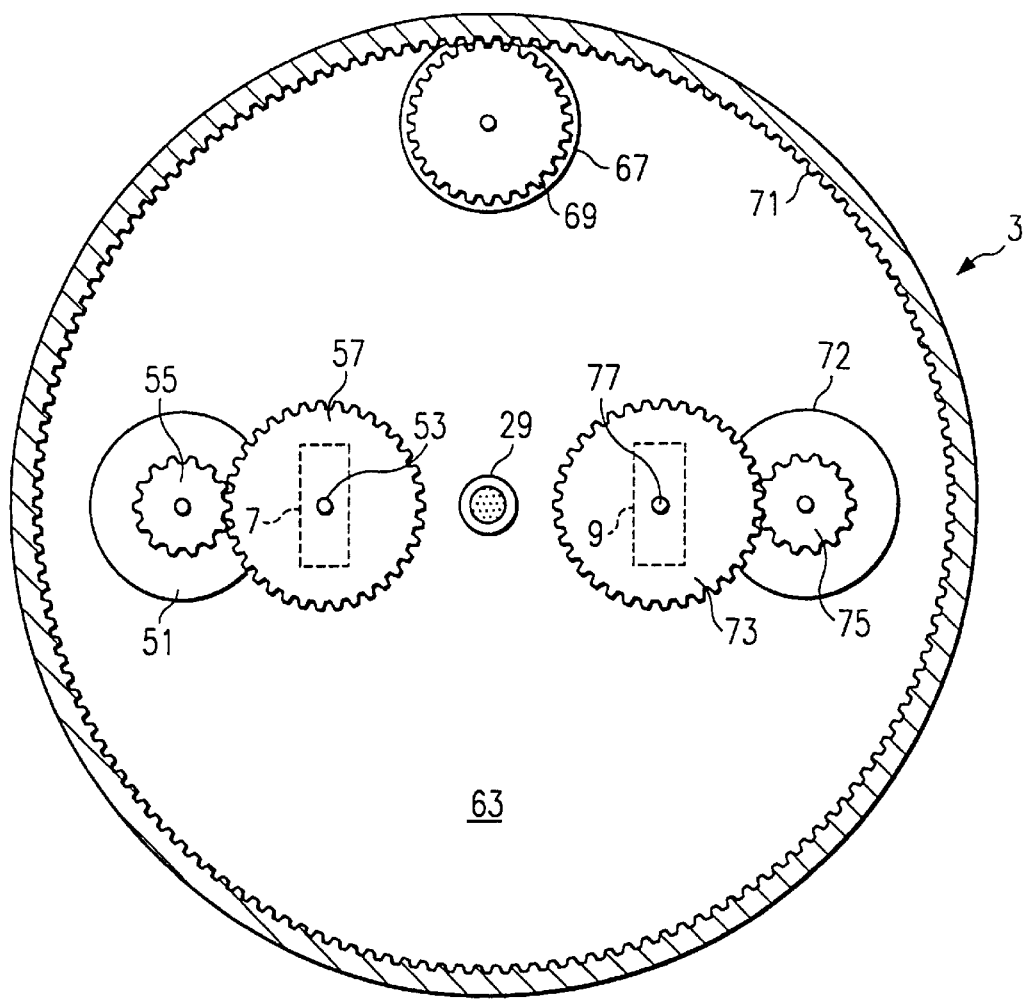
FIG. 5 is a cutaway top view of the upper housing taken through plane 5—5 in FIG. 4.
Figure 6:
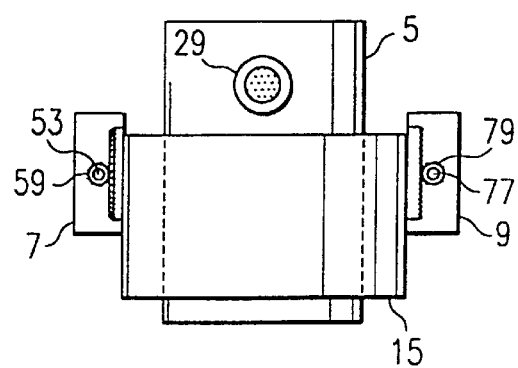
FIG. 6 is an cutaway top view of the lower portion of the imaging device taken through plane 6—6 in FIG. 4.

Referring now to FIGS. 4–6, an elevation motor 51 drives an elevation shaft 53 by means of gears 55, 57. The elevation shaft 53 extends downwardly through the hollow left camera support 7. A ring and pinon gear arrangement 59 at the lower end of the elevation shaft 53 transfers the rotary motion of the elevation shaft 53 to the camera housing 15, thereby causing the camera housing 15 to elevate or depress, depending on the direction of rotation of the elevation motor 51. In this embodiment of the invention, the camera housing 15 can be elevated 70 degrees above and depressed 90 degrees below above a plane perpendicular to the longitudinal axis 27 of the camera and passing through intersection of the longitudinal axis 27 and the focal axis 17 of the camera.

The elevation motor 51 is mounted on a plate 63. The plate 63 is rotably mounted within the upper housing 3 on a bearing 65.

An azimuth motor 67 is also mounted on the plate 63. The azimuth motor 67 drives an azimuth gear 69. The azimuth gear 69 engages a housing gear 71 which is attached to the inner surface of the upper housing 3. When the azimuth motor 67 rotates, the plate 63 rotates within the upper housing 3. In this embodiment, the plate 63 rotates plus or minus 180 degrees in order to minimize the amount the camera cable 21 is twisted. 360 degree rotation can easily be achieved by using conventional slip rings.

A zoom/focus motor 72 drives gears 73, 75, which rotate a zoom/focus shaft 77. The zoom/focus shaft extends downwardly through the right camera support 9. At the bottom of the focus shaft 77, a ring and pinon arrangement 79 transfers the rotary motion of the focus shaft 77 to a zoom lens mechanism (not shown) within the camera housing 5.

Figure 7:
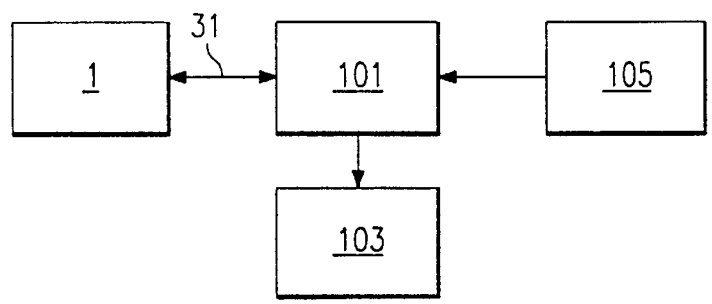
FIG. 7 is a block diagram of a system for controlling the imaging device of FIG. 1 and for displaying the images transmitted by the imaging device.

Referring now to FIG. 7, the imaging device 1 is connected to a control console 101 by means of the imaging device cable 31. Signals from the CCD of the imaging device 1 are amplified by circuits in the control console 101 and directed to a display device 103. In this embodiment of the invention, the display device 103 is a conventional television set.

A foot pedal control assembly 105 allows the surgeon (not shown) to control the imaging device 1. The foot pedal control assembly 105 includes four controls (not shown): (1) camera housing left and right; (2) camera housing up and down; (3) zoom in and out; and (4) light intensity up and down. Signals from the foot pedal control assembly 105 are routed to the control console 101. Circuits (not shown) in the control console 103 convert the control assembly signals into signals which are suitable to control the imaging device 1, then route the converted signals to the imaging device 1.

Figure 8:
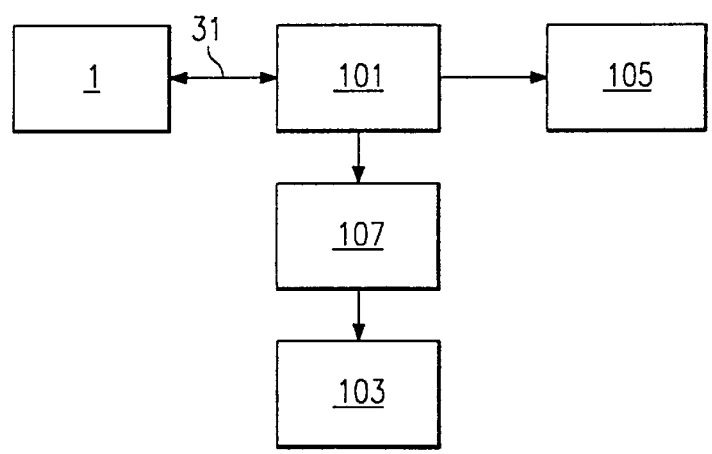
FIG. 8 is a block diagram of a second control and display system for the imaging device of FIG. 1.

In the embodiment of the invention shown in FIG. 8, a computer 107 is interposed between the control console 101 and the display device 103. A plurality of computer programs contained in the computer 107 allow operating team personnel to manipulate and/or store the signals from the imaging device 1.

Figure 10:
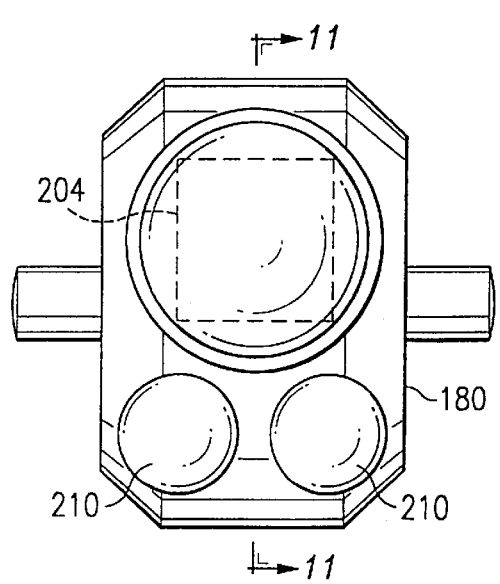
FIG. 10 is a front view of the camera housing shown in FIG. 10.
Figure 11:
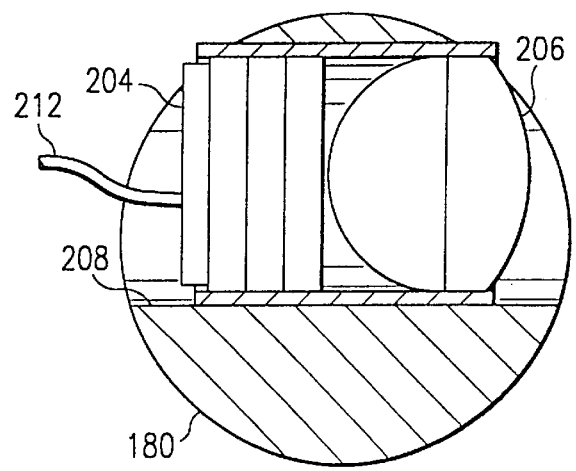
FIG. 11 is a cutaway side view of the camera housing taken through plane 11—11 in FIG. 10.

FIGS. 9–11 illustrate a second surgical/diagnostic imaging device in accordance with the invention. Referring first to FIG. 9, the imaging device comprises two major assemblies: a camera assembly 150 and a disposable sheath assembly 152.

In the camera assembly 150, a rotary stepper motor 154 is rigidly mounted in an upper housing 156. A linear stepper motor 158 and the distal end of a planetary gear assembly 162 are press fitted in a linear stepper motor housing 164. The proximal end of the planetary gear assembly 162 is attached to the upper housing 156 by screws 168.

Three planetary gears 170 (only two of which are shown in FIG. 9) are rotably mounted on pins 172 within the planetary gear assembly 162. The rotary stepper motor 154 drives the planetary gears 170 through a sun gear 174.

The proximal end of a camera support tube 178 is press fitted in the linear stepper housing 164. A camera housing 180 is pivotally mounted between pair of arms 182 (only one of which is shown in FIG. 9) that are integral with and extend from the distal end of the camera support tube 178. The linear stepper motor 158 acts through a pushrod 186 and a fork 188 to control the elevation of the camera housing 180.

The disposable sheath assembly 152 comprises a sheath 190, a sheath housing 192, and a ring gear 194. The distal portion of the sheath 190 is optically clear. The proximal end of the sheath 190 is adhesively attached within the distal end of the sheath housing 192. The ring gear 194 is adhesively attached within the proximal end of the sheath housing 192.

Prior to use, the camera assembly 150 is inserted into the sheath assembly 152, and the planet gears 170 engage the ring gear. As a result, when the rotary stepper motor 154 is actuated, the camera assembly 150 rotates in relation to the longitudinal axis 202 of the sheath assembly.

As is best shown in FIGS. 10 and 11, a CCD assembly 204 and a lens 206 are mounted within a camera bore 208 in the camera housing 180. A pair of high intensity lights 210 are mounted in bores that are coaxial with the camera bore 208.

A multi-conductor flexcable 212 provides the necessary connections for the CCD assembly 204, for the camera housing lights 210, and for three high intensity lights 214 that are disposed in bores in the pushrod 186. The flexcable 212 extends from the camera housing 180 to the upper housing 156. In the upper housing 156, the flexcable 212 is combined with power and control wires (not shown) for the rotary stepper motor 154 and the linear stepper motor 158 to form the camera assembly cable 218. The camera assembly cable 218 passes through an orifice 220 in the upper housing 152. As with the embodiment of the invention shown in FIGS. 1–8, the camera assembly cable 218 connects the camera assembly 150 to external display and control devices (not shown).

What is claimed is:

1. A method for imaging an inner portion of a body of a living being, comprising steps of:

(a) inserting into the body at least a portion of a viewing apparatus including a sheath, a rigid elongated support member extending along a longitudinal axis of and movable relative to or removable from the sheath, and an image sensor movably mounted to a portion of the support member and disposed within the sheath; and (b) moving the image sensor with respect to the portion of the support member and with respect to the sheath so that an imaging axis of the images sensor changes its angular orientation with respect to a longitudinal axis of the support member and passes through different portions of the sheath.

2. The method of claim 1, wherein the step (b) includes a step of moving the image sensor with respect to the portion of the support member while keeping the sheath stationary with respect to the support member.

3. The method of claim 2, further including a step of:

(c) rotating the portion of the support member relative to the sheath, thereby rotating the image sensor relative to the sheath.

4. The method of claim 2, wherein the image sensor is pivotally connected to the portion of the support member along a pivot axis, and wherein the step (b) includes a step of:

(b1) pivoting the image sensor about the pivot axis.

5. The method of claim 4, wherein the step (b1) includes a step of pivoting the image sensor at least ninety degrees about the pivot axis.

6. The method of claim 4, wherein the step (b1) includes a step of pivoting the image sensor at least one hundred degrees about the pivot axis.

7. The method of claim 4, wherein the step (b1) includes a step of pivoting the image sensor at least one hundred and thirty five degrees about the pivot axis.

8. The method of claim 1, further including a step of:

(c) rotating the portion of the support member relative to the sheath, thereby rotating the image sensor relative to the sheath.

9. The method of claim 1, wherein the image sensor is pivotally connected to the portion of the support member along a pivot axis, and wherein the step (b) includes a step of:

(b1) pivoting the image sensor about the pivot axis to orient the imaging axis of the image sensor transverse to the longitudinal axis of the support member.

10. The method of claim 9, wherein the step (b1) includes a step of pivoting the image sensor at least ninety degrees about the pivot axis.

11. The method of claim 9, wherein the step (b1) includes a step of pivoting the image sensor at least one hundred degrees about the pivot axis.

12. The method of claim 9, wherein the step (b1) includes a step of pivoting the image sensor at least one hundred and thirty five degrees about the pivot axis.

13. The method of claim 1, wherein the support member is movable relative to the sheath.

14. The method of claim 1, wherein the support member is removable from the sheath.

15. A method for examining an area within a body of a living being, comprising steps of:

(a) inserting into the body at least a portion of a viewing apparatus including a sheath, a support member extending along a longitudinal axis of and movable relative to or removable from the sheath, and a solid-state image sensor that is disposed within the sheath, the image sensor being movably mounted to the support member; and (b) pivoting the image sensor about a pivot axis and relative to the sheath so that an imaging axis of the image sensor passes through different portions of the sheath and is incident on different portions of the area within the body to enable the area of the body to be reviewed.

16. The method of claim 15 further including a step of:

(c) rotating the support member relative to the sheath, thereby rotating the image sensor relative to the sheath.

17. The method of claim 16, wherein the step (b) includes a step of pivoting the image sensor relative to the sheath while keeping the sheath stationary with respect to the support member.

18. The method of claim 15, wherein the step (b) includes a step of pivoting the image sensor relative to the sheath while keeping the sheath stationary with respect to the support member.

19. The method of claim 15, wherein the step (b) includes a step of pivoting the image sensor at least one hundred degrees about the pivot axis.

20. The method of claim 15, wherein the step (b) includes a step of pivoting the image sensor at least one hundred and thirty five degrees about the pivot axis.

21. The method of claim 15, wherein the step (b) includes a step of pivoting the image sensor at least ninety degrees about the pivot axis.

22. The method of claim 15, wherein the support member is movable relative to the sheath.

23. The method of claim 15, wherein the support member is removable from the sheath.

* * * * *

UNITED STATES PATENT AND TRADEMARK OFFICE
CERTIFICATE OF CORRECTION

PATENT NO.    : 6,007,484
DATED         : December 28, 1999
INVENTOR(S)   : Robert Lee Thompson It is certified that error appears in the above-identified patent and that said Letters Patent is hereby corrected as shown below:

Title page,
Item [54], Title, change the title from: "ENDOSCOPE HAVING ELEVATION AND AZIMUTH CONTROL OF CAMERA" to -- METHOD FOR IMAGING AN INNER PORTION OF A BODY --.
Item [75], Inventors, change the inventor's information from: "Robert Lee Thompson, Dallas, TX" to -- Robert Lee Thompson, Rogers, Ark. --.
Item [73], Assignee, change the designated Assignee from: "Image Technologies Corporation, Rogers, Ark." to -- Pinotage, LLC, Fayetteville, Ark. --.

Signed and Sealed this

Second Day of July, 2002

*Attest:*

JAMES E. ROGAN
*Attesting Officer*        *Director of the United States Patent and Trademark Office*